United States Patent [19]

Fischl et al.

[11] Patent Number: 4,790,814
[45] Date of Patent: Dec. 13, 1988

[54] ARTIFICIAL FERTILIZATION CATHETER

[76] Inventors: Franz H. Fischl, Weimarer Strasse 5/16, A-1180 Vienna; Ewald Pickhard, Redtenbachergasse 15, A-1160 Vienna, both of Austria

[21] Appl. No.: 35,993

[22] Filed: Apr. 8, 1987

[30] Foreign Application Priority Data

Apr. 9, 1986 [AT] Austria .................... 921/86

[51] Int. Cl.⁴ .............................................. A61M 1/00
[52] U.S. Cl. ..................... 604/27; 604/275; 604/55
[58] Field of Search ...................... 604/27, 43, 45, 117, 604/264, 275, 278, 279, 280, 55

[56] References Cited

U.S. PATENT DOCUMENTS

| | | | |
|---|---|---|---|
| 2,036,218 | 4/1936 | Kammer | 604/27 |
| 2,566,632 | 9/1951 | Propp | 604/275 |
| 3,841,304 | 10/1974 | Jones | 128/344 |
| 4,336,801 | 6/1982 | Sentell et al. | 604/279 |
| 4,402,684 | 9/1983 | Jessup | 604/264 |
| 4,592,748 | 6/1986 | Jost | 604/279 |

Primary Examiner—John D. Yasko
Attorney, Agent, or Firm—Kurt Kelman

[57] ABSTRACT

The invention specifies a catheter for artificial fertilization, which is provided with a flexible hose-like catheter section insertible into the uterine cavity of a womb via the cervical cavity. In a terminal portion allocated to a cervical passage, there is provided a conical attachment enlarging rearwardly. A passage in the other terminal portion facing away from the attachment, is closed off at the forward and end, is rounded off or made in spherical cap form. The passage is provided rearwards of the rounded-off terminal portion with two peripherally staggered and radially extending outflow openings. The hose-like catheter section has a flexible hose-like rearward extension extending from the conical attachment. The length of the hose-like extension corresponds substantially to the length of a vagina.

7 Claims, 2 Drawing Sheets

ARTIFICIAL FERTILIZATION CATHETER

BACKGROUND OF THE INVENTION

1. Field of the Invention

The invention relates to a catheter for artificial fertilisation comprising a flexible tubular catheter section insertible into the womb or rather into the uterine cavity via the inner cervical aperture, which is provided within a terminal portion allocated to a cervical passage with a conical attachment increasing towards this extremity and is closed off at the end side in the other terminal portion and rounded off or rather made in spherical cap form and comprising a passage which is connected to a radially positioned outflow opening before the rounded-off terminal portion.

2. Description of the Prior Art

Catheters for artificial fertilisation are already known—according to EP No. A1-122 571—which extend into the uterine cavity from the extremity of the cervical passage facing towards the vagina. A coupling device whereby the catheter passage is connected to the outlet of a syringe is provided in the entry portion of the cervical passage. The syringe is positioned within the vagina and is operated via a lever system from the outside of the vagina, a support means being inserted into the vagina for this purpose. This kind of artificial fertilisation did not provide particularly satisfactory however, because the handling of these different parts is comparatively complex and equally because of the plurality of the individual parts required and also because the equipment required for introduction of the semen cannot be kept wholly sterile, which may increase the risk of infection within the vagina and womb and thereby imperil the success of the inseminating operation.

OBJECTS AND SUMMARY OF THE INVENTION

The present invention has the fundamental object of devising a catheter with which an artificial fertilisation by means of insemination is possible, which is painless to the patient, sterile and does not cause injury.

The affect of the invention is accomplished with a hose-like catheter section having two radially extending outflow openings offset in peripheral direction in a distal terminal portion and a conical attachment at an opposite terminal portion. A flexible tubular extension extends from the conical attachment in a direction opposed to the outflow openings, and has a length substantially corresponding to the length of a vagina. The unexpected advantage of this apparently simple solution consists in that the catheter extends from the entry of the vagina as far as into the uterine cavity and that an unobjectionable semen infeed into the uterine cavity is thus possible. The flexible construction renders it possible despite the strength required for insertion into the cervical passage, that the same may adapt itself without any difficulty to the momentary direction of the cervical passage even in the case of a considerably forwardly or rearwardly deflected position of the uterus. A gentle insertion into the uterine cavity through the inner cervix aperture is thus possible without immobilisation of the cervix. An injury to the mucous membrane in this area and thus possible bleeding is also prevented, and an impediment to the fertilising operation by these flows of blood is thereby precluded. Another substantial advantage of the inventive solution consists in that this sterile one-piece section is provided with two outflow openings within the uterine cavity, thereby preventing a stimulation or irritation or even injury of the mucous membrane within the uterine cavity by the emergence of compressed air, as possible in the case of injection of raw semen or of semen prepared within a variety of nutrient agents by the air bubbles contained therein. The uncontrollable injuries to the mucous membrane which were connected with bleeding and thus with an impairment of the semen quality, which had occurred until now, are prevented thereby and the success rate of artificial insemination is improved by this means.

Provision is made according to another embodiment that the passage of the hose-like extension in the terminal portion facing away from the conical attachment is made in conically widening form, and in particular as a "Luer" cone. It is possible thereby to join the catheter passage direct to a syringe via the hose-like extension, which is facilitated if the passage is shaped in the form of a Luer taper in its terminal portion projecting out of the vagina.

According to another development, it is possible to incorporate an annular and in particular frustoconical bead or enlargement extending coaxially with respect to the bore, between the conical attachment and the hose-like extension. This annular and in particular frustoconical enlargement allows for improved support of the catheter on the entry to the cervical passage, so that an excessively deep insertion of the catheter into the uterine cavity is also prevented during the artificial fertilisation.

It is advantageous if the catheter is produced in one piece and in particular from an elastic plastics material, e.g. polyethylene or polypropylene or soft PVC, since a continuous hermetic connection is thereby provided from the vaginal entry into the uterine cavity during the injection of the semen and the totality of the semen is thereby conveyed into the required portion of the uterine cavity with considerable reliability.

Provision is made according to another embodiment of the invention for the semen outflow opening to be made substantially rectangular and for the width thereof to correspond substantially to a diameter of the passage through the hose-like catheter section, since an excessive pressure upon emergence of the semen from the passage of the catheter is thereby prevented.

Furthermore, it is advantageous if the air outflow opening which is oppositely situated to the semen outflow opening, suitably in mirror symmetry, has a smaller outflow cross-section since the pressure of the compressed air contained in the pure semen or semen prepared in nutrient solutions during the injection prior to the total ejection of the semen from the catheter passage is reduced by the oppositely situated relief opening and a pressure surge caused by excessively compressed air and thus a consequent irritation of the mucous membrane is thereby prevented.

It is possible for the air outflow opening of the hose-like catheter section to be formed by an air-permeable portion in the hose which is situated opposite to the semen outflow opening, thereby retaining a specific outflow direction of the semen whilst nevertheless preventing perforations caused by air inclusions in the semen.

It is possible for the diameter of the hoselike catheter section to be approximately half of the diameter of the hose-like extension, thereby facilitating the insertion of the catheter portion extending from the outflow opening to the area of the concial attachment, into the uterine cavity.

BRIEF DESCRIPTION OF THE DRAWINGS

The invention will now be described, by way of example, with reference to the following partly diagrammatic drawings, in which.

DETAILED DESCRITION OF THE PREFERRED EMBODIMENT

Figure 1:
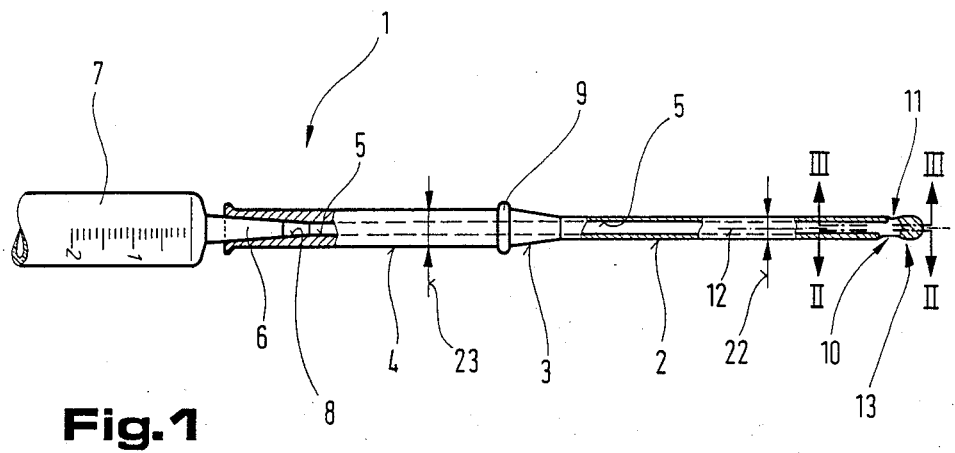
FIG. 1 is a partly sectional elevation of catheter according to the invention with a syringe attached thereto.

FIG. 1 shows a catheter 1 for artificial insemination which comprises a flexible hose-like catheter section 2, an attachment 3 joined thereto and of generally frustoconical form tapering forwardly, and a hose-like extension 4 extending rearwardly from the conical attachment 3 in the direction away from the hose-like catheter section 2. The hose-like catheter section 2, the attachment 3 and the extension 4 consist of a flexible and pharmacologically acceptable plastics material, for example polyethylene, polypropylene, soft PVC or an appropriate polyurethane. Internal passage 5 traveike catheter section 2, an attachment 3 joined thereto and of generally frustoconical form tapering forwardly, and a hose-like extension 4 extending rearwardly from the conical attachment 3 in the direction away from the hose-like catheter section 2. The hose-like catheter section 2, the attachment 3 and the extension 4 consist of a flexible and pharmacologically acceptable plastics material, for example polyethylene, polypropylene, soft PVC or an appropriate polyurethane. Internal passage 5 traverses catheter section 2, the concial attachment 3 and the hose-like extension 4. In the rearward terminal portion of the extension 4 facing away from the conical attachment 3, the passage 5 is provided with a Luer taper 8 widening in the direction towards a syringe 7 for reception of an attachment member 6 of the syringe 7. This allows standardised throwaway syringes to be directly attached to the catheter 1. Furthermore, an annular enlargement or rim 9, which may also be constructed as a cone frustum, is situated at the extremity of the conical attachment 3 facing towards the extension 4.

Outflow openings 10,11 extending radially, i.e. at right angles to the longitudinal axis of the passage 5 are situated at the distal terminal portion of the hose-like catheter section 2. As also apparent, the passage 5 terminates a little short of the extremity of the hose-like catheter section 2, and this extremity 13—is rounded off spherically.

Figure 2:
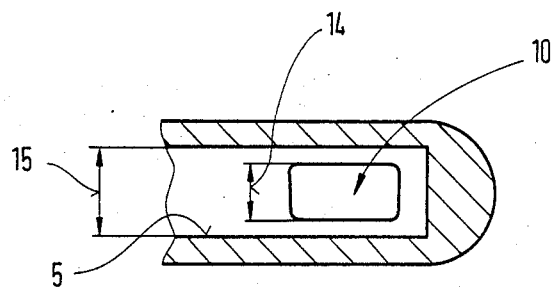
FIG. 2 is a fragmentary cross-section, on an enlarged scale, through the catheter in a terminal portion defining the outflow openings, along the lines II—II in FIG. 1.

As more clearly apparent from FIG. 2, the semen outflow opening 10 has a comparatively large cross-section, and a generally rectangular form. Width 14 of the outflow opening 10 corresponds approximately to diameter 15 of the passage 5.

Figure 3:
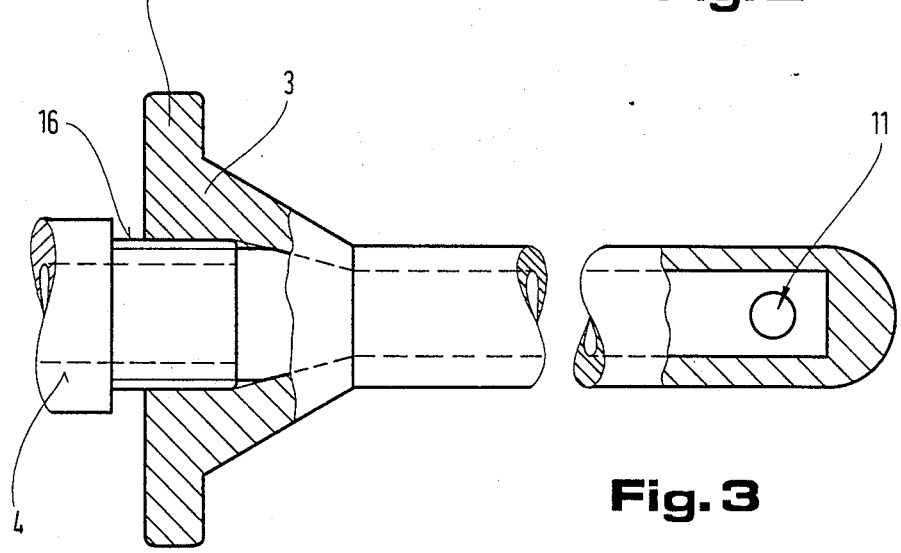
FIG. 3 is a like fragmentary cross-section along the lines III—III in FIG. 1, showing that terminal portion as well as a connecting device between the hose-like catheter section and the hose-like extension at the opposite terminal portion.

In FIG. 3 is shown the air outflow opening 11 diametrically oppositely situated to the outflow opening 10, which—for example—has a circular cross-section of a smaller outflow cross-section than the outflow opening 10. The outflow openings 10,11 may have any desired shape other than rectangular or circular, and they may be staggered in different radial directions, for example at an angle of 30° or 60°.

As also shown in purely diagrammatical manner in FIG. 3, it is also possible for the extension 4 to be installed releasably in the concial attachment 3. It is possible for example that the extension 4 may be screwed into the conical attachment 3 by means of a screwthread 16, prior to insertion of the catheter. In the same way, it is evidently also possible to make use of any snap-in joint or clam-ring joint or the like, to allow for securing a hermetic connection of the hose to the conical attachment 3.

Figure 4:
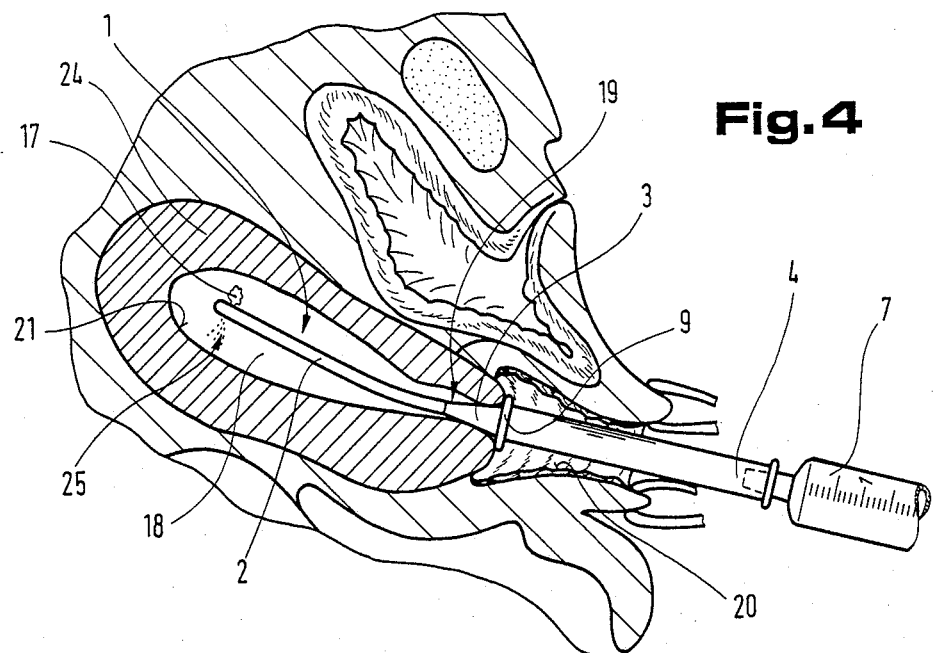
FIG. 4 shows the catheter in the position inserted into the uterine cavity with the womb in sideview and sectioned.

In FIG. 4, the catheter 1 is shown in its operative position for introduction of semen 17 from the syringe 7 into the uterine cavity 18.

As perceptible, the conical attachment 3 bears with the annular rim 9 on the entry of the cervical passage 19 and assures a satisfactory seal of the uterine cavity 18 as well as a satisfactory support for the extension 4 extending through the vagina 20. The hose-like catheter section 2 of the catheter 1 is thereby prevented from being inserted too far into the uterine cavity 18 and irritating or injuring the mucous membrane 21 during the injection of the semen 17 by means of the syringe 7. It is known that, if the mucous membrane 21 is injured, blood discharges occur within the uterine cavity, thereby destroying the semen introduced and preventing a fertilisation.

The advantage offered by a different diameter 22, FIG. 1, of the hose-like catheter section 2 and diameter 23 of the extension 4 is also more clearly apparent from this illustration. In view of the larger diameter 23 of the extension 4, the catheter 1 is more rigid in the area of the vagina 20, thereby promoting an insertion of the more flexible hose-like catheter section 2 into the uterine cavity 18 though the cervical passage 19. On the other hand, there is hardly any risk of the mucous membrane 21 being injured within the uterine cavity 18 or in the area of the cervical passage 19, thanks to the high flexibility of the hose-like catheter section 2.

Figure 5:
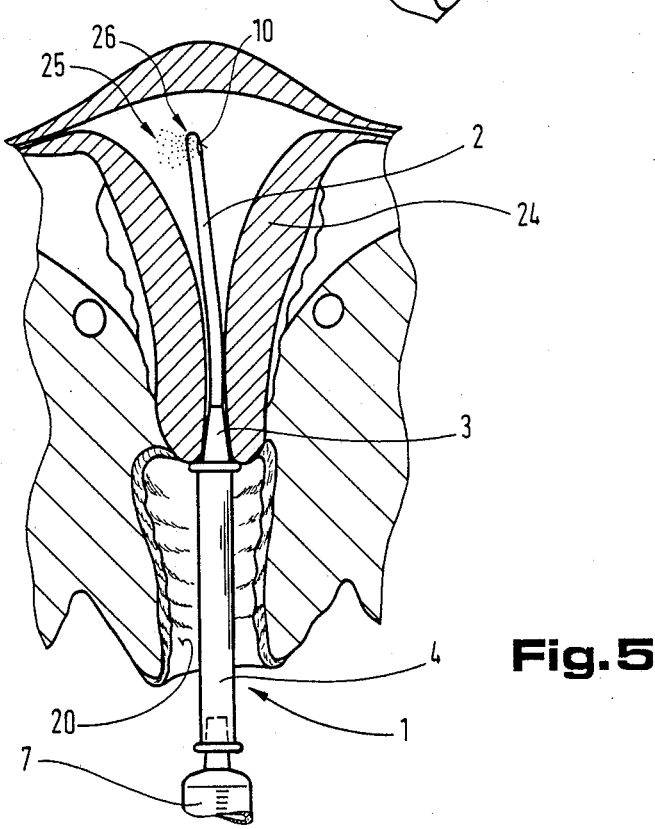
FIG. 5 shows the catheter in the position of insertion into the uterine cavity, with the womb in end view and cross-sectioned.

The position of the inserted catheter 1 in the vagina is equally apparent in the front view of the womb 24, in FIG. 5. Instead of the air outflow opening 11, air 25 separating from the semen 17 may simply pass out through an air-permeable area 26 situated opposite to the outflow opening 10 as diagrammatically shown in FIG. 5.

As apparent from the illustrations in FIGS. 4 and 5, it is thus possible for the syringe 7 intended for introduction of the semen 17 though the catheter to be placed outside the vagina 20, and to operate in wholly sterile manner by this means. As also indicated digrammatically in FIG. 4, the arrangement of the semen and air outflow openings 10 and 11 or of the air-permeable area 26 shown in FIGS. 1 to 3 and 5 establishes the possibility that compressed air 25 contained in air bubbles of the semen may escape under lower pressure though the outflow opening 11 acting as a relief bore or through the air-permeable area 26, thereby further reducing the risk of injury to the mucous membrane 21.

It is believed that the invention and many of its attendant advantages will be understood from the foregoing description, and it will be apparent that various changes may be made in the form, construction and arrangement of the parts without departing from the spirit and scope of the invention or sacrificing all of its material advantages, the form hereinbefore described merely being preferred embodiments.

We claim:

1. A catheter for artificial insemination, which comprises
    (a) a flexible hose-like catheter section defining a longitudinally extending internal passage and having a first terminal portion and a second, distal terminal portion opposite the first terminal portion, the distal terminal catheter section portion having
        (1) a rounded-off closed extremity and
        (2) two peripherally staggered radial outflow openings of different-sized outflow cross sections, one of the outflow openings being larger for outflow of semen and the second outflow opening being smaller for outflow of air,
        (3) the hose-like catheter section having a length enabling the hose-like catheter section to be inserted into a uterine cavity,
    (b) an impermeable flexible hose-like extension defining a longitudinally extending internal passage in alignment with the internal passage in the hose-like catheter section and having a terminal portion adjoining the first terminal portion of the catheter section,
        (1) the hose-like extension having a length corresponding substantially to the length of a vagina, and
    (c) a concial attachment at the first terminal portion of the hose-like catheter section and tapering inwardly towards the distal terminal portion thereof or attaching the hose-like extension to the hose-like catheter section, the conical attachment
        (1) having an internal passage in communication with the internal passages in the hose-like catheter section and extension, and
        (2) fitting into a cervical opening leading from the vagina into the uterine cavity.

2. The catheter of claim 1, wherein the internal passage in the hose-like extension is conically widened at a terminal portion thereof opposite the terminal portion adjoining the first terminal portion of the catheter section.

3. The catheter of claim 1, wherein the conical attachment comprises an annular rim between the adjoining terminal portions.

4. The catheter of claim 1, wherein the semen outflow opening is substantially rectangular and has a width corresponding substantially to the diameter of the internal passage.

5. The catheter of claim 1, wherein the two outflow openings are opositely situated in mirror symmetry.

6. The catheter of claim 1, wherein the air outflow opening is an air-permeable area of the hose-like catheter section diametrically opposite the semen outflow opening.

7. The catheter of claim 1, wherein the hose-like catheter section has a diameter approximately half as large as that of the hose-like extension.

* * * * *